(12) United States Patent
Choudary et al.

(10) Patent No.: US 6,620,981 B1
(45) Date of Patent: Sep. 16, 2003

(54) PROCESS FOR THE PREPARATION OF NITROTOLUENES

(75) Inventors: Boyapati Manoranjan Choudary, Andhra Pradesh (IN); Mannepalli Lakshmi Kantam, Andhra Pradesh (IN); Kompella Vishweshwar Ramprasad, Andhra Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/103,646

(22) Filed: Mar. 20, 2002

(51) Int. Cl.⁷ ............................................. C07L 205/00
(52) U.S. Cl. ..................................................... 568/940
(58) Field of Search ......................................... 568/940

(56) References Cited

U.S. PATENT DOCUMENTS

| | | | |
|---|---|---|---|
| 4,234,470 A | 11/1980 | Lawrence | 568/939 |
| 4,325,845 A * | 4/1982 | Lim | |
| 4,418,230 A | 11/1983 | Bakke et al. | 568/940 |
| 4,665,252 A * | 5/1987 | Hoelderich | |
| 5,102,530 A | 4/1992 | Edwards et al. | 208/120 |
| 5,710,085 A | 1/1998 | Absil et al. | 502/68 |
| 6,034,287 A | 3/2000 | Choudary et al. | 568/927 |
| 6,376,726 B1 * | 4/2002 | Choudary | |

FOREIGN PATENT DOCUMENTS

EP    1 004 570 A1    5/2000

OTHER PUBLICATIONS

"Kirk–Othmer Encyclopedia of Chemical Technology", 4$^{th}$ Ed., vol. 16, pp. 889–925 (1995).*
Keith Smith et al., *Chem. Comun.*, 1996, 469–470.
B.M. Choudary et al., *Chem. Comm.*, 2000, 25–26.
Francis J. Walker et al., *Chem. Comm.*, 1997, 613–614.
European Search Report (2002).
Haouas et al., *Chemical Abstract*, 2001, 134(13).

* cited by examiner

*Primary Examiner*—Michael L. Shippen
(74) *Attorney, Agent, or Firm*—Morgan & Finnegan, LLP

(57) ABSTRACT

The present invention relates to a process for the preparation of nitrotoluenesl. More particularly, the present invention relates to a process for the preparation of nitrotoluenes with high para -selectivity from toluene using zeolite beta with different binders as a catalyst.

24 Claims, No Drawings

PROCESS FOR THE PREPARATION OF NITROTOLUENES

FIELD OF THE INVENTION

The present invention relates to a process for the preparation of nitrotoluenes. More particularly, the present invention relates to a process for the preparation of nitrotoluenes with high para -selectivity from toluene using zeolite beta with different binders as a catalyst

BACKGROUND OF THE INVENTION

Nitration process is used for the production of many large-volume chemicals such as nitrotoluenes, nitrochlorobenzenes and other nitroarenes which are vital intermediates for dyes, pharmaceuticals, perfumes and pesticides. Nitration of arenes is performed classically with a mixture of nitric acid and sulfuric acids. Major disadvantages in this method are formation of by-products of polynitration and environmental pollution during in disposal of spent acid.

Reference is made to U.S. Pat. No. 4,418,230 wherein a method for nitration of toluene with $HNO_3$ and $H_2SO_4$ at 0 to 52° C. is described (o:m:p 55:2.3:38.9). The drawbacks are the use of sulfuric acid and also the formation of more of o-isomer.

Reference is made to another U.S. Pat. No. 1,12,006 wherein a process for the nitration of toluene with $HNO_3$ and 10% $H_2SO_4$ impregnated $Al_2O_3$ and 1% Mo at 135–145° C./20 torr is described (o:m:p 34.0:3.5:62.5). The drawbacks of this disclosure are the use of sulfuric acid in the preparation of the catalyst and the deactivation of the catalyst on each cycle.

Although it is known that benzene and its homologues can be nitrated with $HNO_3$ alone without using sulfuric acid, little or no progress has been made in this direction on a commercial scale. The disadvantage of this method is low productivity and the use of large excess of nitric acid (molar ratio of nitric acid to benzene 2:1to 4:1) which increases the possibility of formation of polynitro compounds and affects the economics of the project. Recently attention has been focussed on the development of environmentally friendly solid acid catalysts such as Nafion especially in Friedel-Crafts reactions to replace environmentally hazardous sulfuric acid in nitration reactions.

Reference is made to U.S. Pat. No. 4,234, 470 wherein a method for nitration of benzene, chlorobenzene and toluene with $HNO_3$ in presence of Nafion catalyst is described. The drawbacks are the use of expensive Nafion resin whose activity decreases on each cycle and offers nearly identical isomer selectivity (o:m:p 56:4:40) as that of mixed acid.

Reference is also made to *Chem. Commun*, 469, 1996 wherein benzene, alkylbenzenes and halobenzenes are nitrated in quantitiative yields and with high para-selectivity in a solvent free process by using stiochiometric quantity of nitric acid and acetic anhydride at 0 to 20° C. in the presence of zeolite. beta, a recyclable catalyst.

Reference is made to *Chem. Commun*. 613, 1997 wherein aromatics are nitrated in good yields in dichloromethane solvent by using stiochiometric quantities of 69% nitric acid at reflux temperature of the solvent in the presence of lanthanide (111) triflates as recyclable catalysts. The drawbacks are the slowness of the reaction, more time being required for completion of the reaction, the use of expensive catalysts and low productivity of the process. The isomeric ratio is also identical with that of mixed acids.

Reference is made to U.S. Pat. No. 6,034,287 and publication *Chem. Commun*. 25, 2000, wherein process for the production of nitroarenes with high para-selectivity from monosubstituted aromatic hydrocarbons using aluminosilicates as catalysts is described. The drawbacks are the catalyst is in powder form and can not be used in the fixed bed.

OBJECTS OF THE INVENTION

It is an object of the present invention to provide a simple and an ecofriendly process for production of substituted nitroarenes.

It is another object of the invention to provide a simple method for obtaining nitrotoluenes with high para-selectivity.

It is still another object of the invention to provide a process for obtaining nitrotoluenes using a zeolite beta catalyst with binders to impart robustness to the zeolite beta catalyst to withstand vagaries of the reacting substrate and nitric acid on a catalytic fixed bed.

It is another object of the invention to provide a process for the preparation of nitrotoluenes wherein the use of sulfuric acid, a hazardous chemical and expensive acetic anhydride which forms an explosive mixture in conjunction with nitric acid is dispensed with.

It is still another object of the invention to provide a process for the preparation of nitrotoluenes wherein the problem of effluent disposal is obviated.

SUMMARY OF THE INVENTION

The above and other objects are achieved by the present invention wherein nitrotoluenes are produced with high para-selectivity using a zeolite beta catalyst in an inorganic/organic matrix in the absence of acetic anhydride and sulfuric acid.

Accordingly, the present invention provides a process for the preparation of nitrotoluenes with high para selectivity from toluene which comprises nitrating toluene with nitric acid in the presence of a catalyst system comprising Zeolite beta and an inorganic/organic matrix, and recovering the desired product.

In one embodiment of the invention the zeolite beta catalyst has an Si/Al ratio in the range of 15/1 to 22/1.

In another embodiment of the invention, the catalyst system is used in the form of powder, pellets, extrudates or spherules.

In another embodiment of the invention, the nitration of toluene is carried out in the absence of sulfuric acid.

In another embodiment of the invention, the nitration of toluene is carried out in the absence of acetic anhydride.

In still another embodiment of the invention, the inorganic matrix is selected from the group consisting of montmorillonite, silamanite and kaolin clay.

In a further embodiment of the invention, the inorganic/organic matrix comprises one or more of graphite, gelatin, acetic acid, polyvinyl alcohol (5–10%), sodium silicate, TEOSI, alumina, stearic acid and acrylate.

In another embodiment of the invention, sodium silicate is used as a binder along with clay in the inorganic matrix.

In another embodiment of the invention, the binder system comprises of graphite and acetic acid.

In another embodiment of the invention, the zeolite beta and binder catalyst system is used in the form of pellets after mixing with the binders.

In another embodiment of the invention, the amount of the inorganic matrix in the catalyst system is in the range of 1.5–20% of the weight of the catalyst system.

In a further embodiment of the invention, the catalyst system pellets measure 6–8 mm diameter and 4–6 mm long.

In a further embodiment of the invention, the pellet bulk density is in the range of 0.25–0.55 gm/cc.

In a further embodiment of the invention, the pellet crushing strength ranges between 0.5–5 kg.

In another embodiment of the invention, the temperature of the nitration reaction is in the range of 100–200° C. preferably 100–160° C.

In a further embodiment of the invention, the selectivity to para-nitrotoluene is >60%.

In another embodiment of the invention, the molar ratio of nitric acid and aromatic is in the range from 0.25 to 2.5, desirably 0.5 to 2.0.

In another embodiment of the invention, nitration is carried out in continuous mode.

In another embodiment of the invention, the nitration is carried out in batch mode. In a further embodiment of the invention, the nitration is carried out over a fixed catalyst bed.

In another embodiment of the invention, the selectivity to para-nitrotoluene ranges from 59–68 in batch mode and 55–61 on a catalytic fixed bed depending on the binder used.

In another embodiment of the invention, the zeolite beta with binder acts as a bifunctional catalyst generating electrophile, nitronium ion as well as instant adsorbent for water formed during the reaction to facilitate electrophilic substitution on toluene.

DETAILED DESCRIPTION OF THE INVENTION

The present invention provides a process for the production of nitrotoluenes with high para-selectivity from toluene by beta zeolite with a Si/Al ratio in the range of 15/1 to 22/1 as a catalyst with an inorganic/organic matrix employed to formulate powder, pellets, extrudates, spherules robust enough to withstand the vagaries of the reacting substrate and nitric acid over the catalytic fixed bed.

The Si/Al ratio is in the range of 15/1 to 22/1 in zeolite beta. The type of zeolite and the Si/Al ratio is important in achieving high para selectivity. While the catalyst zeolite beta can be used alone, mixing with an inorganic or organic matrix provides strength to the catalyst system without significant loss of selectivity to para-nitrotoluene or loss of catalytic activity. The inorganic matrix is preferably a montmorillonite, silamanite or kaoline clay and sodium silicate. The zeolite beta is made into pellets after mixing with the binders. Preferably, the pellets measure 6–8 mm diameter and 4–6 mm long, have a bulk density of 0.25 –0.55 gm/cc, and a crushing strength in the range of 0.5 –5 kg.

The binder imparts robustness to the catalyst to withstand the vagaries of the reacting substrate and nitric acid on a catalytic fixed bed. Beta zeolite mixed with clay and sodium silicate withstands the vagaries of the reacting substrates without any deterioration which was studied up to 200 h.

The nitric acid used as the nitrating agent should normally have a concentration in the range of 50 to 90% (W/V) desirably 60 to 70%. The nitration is effected at a temperature in the range of 100–200° C. preferably 100 –160° C. The selectivity to para nitrotoluene is >60%. The recovery of nitrotoluenes is carried out using conventional methods.

In another embodiment of the present invention the mono-substituted benzene used is toluene. The use of zeolite beta as solid catalyst dispenses the use of hazardous sulfuric acid. The solid acid catalysts used here act as bifunctional catalysts generating electrophile ntironium ion as well as instant adsorbent for water formed during the reaction to facilitate electrophilic substitution on toluene.

Continuous method reactions were performed on a fixed bed containing the catalyst. Before the reaction, the catalyst was calcined at 500° C. for 6 h in a flow of air. Aqueous nitric acid and toluene are pumped from the top with a flow rate of 5 mn/h and 10 ml/h respectively, using syringe pumps with $N_2$ as a carrier gas in to a packed bed with the catalyst in a column type reactor at 160° C. The reaction was conducted continuously.

Toluene and the catalyst were taken in a two necked round bottomed flask equipped with a Dean-Stark apparatus. After the flask was heated to the required temperature, nitric acid was added dropwise in to the reaction mixture over the required period. Simultaneously, the water collected in the Dean-Stark apparatus formed from the reaction was removed continuously. After completion of the reaction, the catalyst was filtered and the reaction mixture was concentrated to obtain the mixture of nitrotoluenes. The molar ratio of nitric acid and aromatic should normally be in the range from 0.25 to 2.5, desirably 0.5 to 2.0. Nitration reaction temperature should normally be in the range from 30 to 190° C., desirably from 80 to 160° C. Nitration process was accomplished in a period of 0.25 to 5.0 h, preferably about 0.5 to 3.0 h.

SCIENTIFIC EXPLANATION

The principal object of the present invention by processing under the above conditions, therefore, was to produce cost effective predominantly para-selective product over the previously reported works. It was achieved because of the possible restricted pore sizes of the aluminosilicates used as solid acid catalysts and also the methodology used in this process. This process dispenses the use of sulfuric acid which totally eliminates the disposal of salts formed consequent to the neutralisation of sulfuric acid.

The production of para-nitrotoluenes with enhanced selectivity over the ortho products which is described here is prompted by market driven research, since the para nitrotoluenes are in greater demand. It also minimises effluents, requires very small amount of water for washings and is non-corrosive in nature, in contrast to the process practiced currently in industry with sulfuric acid. This is an improved and cost effective process with enhanced selectivity of para-nitrotoluene over conventional sulfuric acid process currently under practice in industry, employing small amount of catalyst with binders.

The novelty of the present invention with respect to the prior art is to produce predominantly p-isomer in the nitration of toluene using beta zeolite with a Si/Al ratio in the range of 15/1 to 22/1 as catalyst with an inorganic/organic matrix employed to formulate powder, pellets, extrudates, spherules robust enough to withstand the vagaries of the reacting substrate and nitric acid over the catalytic fixed bed as a solid acid catalyst replacing the hazardous sulfuric acid employed in more than stoichiometric quantities.

The binder. provides strength for beta zeolite required for continuous scale operation. The para-selectivity of beta zeolite with inorganic binders is enhanced both in batch as well as in continuous mode. Beta zeolite with sodium silicate binder is stable up to 20 h in continuous mode but when it is mixed with clay, sodium silicate, the catalyst withstands the vagaries of the reacting substrates without any deterioration which was studied up to 200 h. It shows that the mixture of sodium silicate and clay are the best materials for making beta zeolite pellets with maximum strength.

The activity of the formulated zeolite in spite of the dilution by 10% clay is almost same as displayed by the zeolite without binders. This shows that the clay which has been used as binder must have contributed too towards activity. Indeed, it is known that acidic sites of clay show nitration activity, which is in consonance with our earlier results. (JCS Chem.Commun. 25, 2000). Hence, no visible diffusional hindrance in such a complex situation was detected. On the other hand beta zeolite with the other binders show reduced activity. It is believed that this is due to both diffusional and dilution effects.

Selectivity is possible by the use of solid acids of compatible pore dimensions designed and modified to direct the electrophile, nitronium ion to substitute at the para-position in preference to ortho-position. The solid acid catalysts used here act as bifunctional catalysts generating electrophile, ntironium ion, as well as instant adsorbent for water formed during the reaction to facilitate electrophilic substitution on toluene.

The following examples are given by way of illustration of the present invention and therefore should not be construed to limit the scope of the present invention.

EXAMPLE 1

BATCH METHOD

A mixture of toluene (170 ml) and beta zeolite (10 g) with binder were taken in a 1 litre four-necked glass reactor fitted with a mechanical stirrer and a Dean-Stark apparatus. Temperature of the oil bath was raised to 140° C. Then 60% of aqueous nitric acid (120 ml) was added drop-wise (60 ml/h) with the help of infusion pump to the mixture. The reaction mixture was continued to reflux and the water formed was collected in the Dean-Stark apparatus, which usually takes 1 h. After completion of the reaction (monitored by GC), the catalyst was filtered and the filtrate was washed with sodium bicarbonate solution to remove the unreacted nitric acid and separated the organic and aqueous layers. The organic layer obtained was concentrated to get the pure product.

EXAMPLES 1 TO 13

The procedure was followed as in example 1 and the results are presented in Table 1.

TABLE 1

Para - Selective Nitration of Toluene by beta zeolite with different binders
BATCH MODE REACTION

| Example | Catalyst Binder | Conversion (%) | % of product distribution | | | |
|---|---|---|---|---|---|---|
| | | | O | M | P | Other |
| 1 | Without binder | 57 | 30 | 3 | 65 | 2 |
| 2 | Gelatin | 40 | 31 | 3 | 63 | 3 |
| 3 | Graphite | 40 | 33 | 3 | 60 | 4 |
| 4 | Graphite + Acetic Acid | 46 | 33 | 3 | 60 | 4 |
| 5 | Poly-Vinyl Alcohol (5%) | 40 | 36 | 4 | 60 | — |
| 6 | Poly-Vinyl Alcohol (10%) | 35 | 32 | 5 | 59 | 4 |
| 7 | Acetic Acid | 42 | 29 | 3 | 67 | 1 |
| 8 | Sodium Silicate | 35 | 34 | 4 | 60 | 2 |
| 9 | Sodium Silicate + clay | 55 | 29 | 3 | 64 | 4 |
| 10 | TEOSI | 48 | 29 | 3 | 68 | — |
| 11 | Alumina | 56 | 28 | 3 | 68 | 1 |
| 12 | Stearic Acid | 45 | 31 | 4 | 62 | 3 |
| 13 | Acrylate | 45 | 33 | 4 | 62 | 1 |

EXAMPLE 14

CATALYTIC FIXED BED REACTION

Continuous method reactions were performed on a fixed bed containing the catalyst. Before the reaction, the catalyst was calcined at 500° C. for 6 h in a flow of air. Aqueous nitric acid and toluene are pumped from the top with a flow rate of 5 ml/b and 10 ml/h respectively, using syringe pumps with $N_2$ as a carrier gas in to a packed bed with the catalyst in a column type reactor at 160° C. The reaction was conducted continuously and the conversion was followed by GC.

EXAMPLES 14 TO 22

The procedure was followed as in example 2 and the results are presented in Table 2.

TABLE 2

Para - selective nitration of toluene by beta zeolite with different binders
CONTINUOUS MODE REACTION ON A FIXED BED

| Ex. No | Catalyst Binder | Duration (h) | Bulk density (gm/cc) | Shape & Size (mm) | Crushing strength (Kg) | % of p-nitro toluene in reaction mixture |
|---|---|---|---|---|---|---|
| 14 | Without binder | 35 | 0.25 | 6 × 4 | 0.5 | 65 |
| 15 | Gelatin | 26 | 0.25 | 6 × 4 | 0.5 | 56.00 |
| 16 | Graphite | 8 | 0.35 | 6 × 3 | 0.9 | 55.00 |
| 17 | Graphite + Acetic Acid | 160 | 0.40 | 6 × 4 | 1.5 | 58.00 |
| 18 | Acetic Acid | 33 | 0.40 | 6 × 4 | 1.5 | 60.00 |
| 19 | Sodium Silicate | 20 | 0.41 | 6 × 4 | 1.5 | 60.00 |
| 20 | Sodium Silicate + | 200* | 0.55 | 6 × 4 | 1–4 | 61.00 |

TABLE 2-continued

Para - selective nitration of toluene by beta zeolite with different binders
CONTINUOUS MODE REACTION ON A FIXED BED

| Ex. No | Catalyst Binder | Duration (h) | Bulk density (gm/cc) | Shape & Size (mm) | Crushing strength (Kg) | % of p-nitro toluene in reaction mixture |
|---|---|---|---|---|---|---|
| | clay | | | | | |
| 21 | TEOSI | 50 | 0.41 | 6 × 4 | 1–5 | 60.0 |
| 22 | Poly vinyl alcohol | 10 | 0.40 | 6 × 4 | 1.5 | 55.0 |

*This was tried for the stipulated time and no disintegration of the pellets was detected in the fixed bed The main advantages of the present invention are:
1. A simple method and an ecofriendly process for production of substituted nitroarenes was developed.
2. A simple method for obtaining nitrotoluenes with high para-selectivity was developed.
3. Binders impart robustness to the zeolite beta catalyst to withstand the vagaries of the reacting substrate and nitric acid on a catalytic fixed bed.
4. The use of sulfuric acid, a hazardous chemical is dispensed with.
5. The use of an expensive acetic anhydride which forms an explosive mixture in conjunction with nitric acid, is also dispensed with.
6. The present process is environmentally safe since there is no effluent disposable problem.

We claim:

1. A process for the preparation of nitrotoluenes with high para selectivity from toluene which comprises nitrating toluene with nitric acid in the presence of a catalyst system comprising Zeolite beta and a binder comprising an organic compound selected from the group consisting of gelatin, acetic acid, polyvinyl alcohol, stearic acid, and methyl acrylate; and an inorganic matrix selected from the croup consisting of graphite, sodium silicate, tetraethyl orthosilicate (TEOSI), alumina, and clay and recovering nitroluene.

2. A process as claimed in claim 1 wherein the zeolite beta catalyst has an Si/Al ratio in the range of 15/1 to 22/1.

3. A process as claimed in claim 1 wherein the catalyst system is used in the form of powder, pellets, extrudates or spherules.

4. A process as claimed in claim 1 wherein the nitration of tolulene is carried out in the absence of sulfuric acid.

5. A process as claimed in claim 1 wherein the nitration of tolulene is carried out in the absence of acetic anhydride.

6. A process as claimed in claim 1 wherein the clay is selected from the group consisting of montmorillonite, silamanite and kaolin clay.

7. A process as claimed in claim 1 wherein sodium silicate is used as a binder along with clay in the inorganic matrix.

8. A process as claimed in claim 1 wherein the binder comprises graphite and acetic acid.

9. A process as claimed in claim 1 wherein the catalyst system is used in the form of pellets after mixing the zeolite beta with the binders.

10. A process as claimed in claim 1 wherein the amount of the inorganic compound is in the range of 1.5–20% of the weight of the catalyst system.

11. A process as claimed in claim 9 wherein the pellets measure 6–8 mm in diameter and 4–6 mm long.

12. A process as claimed in claim 9 wherein the pellet bulk density is in the range of 0.25–0.55 gm/cc.

13. A process as claimed in claim 9 wherein the pellet crushing strength ranges between 0.5–5 kg.

14. A process as claimed in claim 1 wherein the temperature of the nitration reaction is in the range of 100–200° C.

15. A process as claimed in claim 14 wherein the temperature of the nitration reaction is in the range of 100–160° C.

16. A process as claimed in claim 1 wherein the selectivity to para-nitrotoluene is >60%.

17. A process as claimed in claim 1 wherein the molar ratio of nitric acid to toluene is in the range from 0.25 to 2.5.

18. A process as claimed in claim 1 wherein the molar ratio of nitric acid an to toluene is in the range from 0.5 to 2.0.

19. A process as claimed in claim 1 wherein the nitration is carried out in continuous mode.

20. A process as claimed in claim 1 wherein the nitration is carried out in batch mode.

21. A process as claimed in claim 1 wherein the nitration is carried out over a fixed catalyst bed.

22. A process as claimed in claim 20 wherein the selectivity to para-nitrotoluene ranges from 59–68 in batch mode depending on the binder used.

23. A process as claimed in claim 22 wherein the selectivity to para-nitrotoluene ranges from 55–61 in a catalytic fixed bed depending on the binder used.

24. A process as claimed in claim 1 wherein the concentration of the nitric acid is in the range of 60 to 70%.

* * * * *